(12) United States Patent
Makhynya et al.

(10) Patent No.: US 10,351,518 B2
(45) Date of Patent: Jul. 16, 2019

(54) METHOD FOR THE PROVISION OF CARBON DIOXIDE FOR THE SYNTHESIS OF UREA

(71) Applicants: THYSSENKRUPP INDUSTRIAL SOLUTIONS AG, Essen (DE); thyssenkrupp AG, Essen (DE)

(72) Inventors: Yevgeny Makhynya, Mülheim an der Ruhr (DE); Joachim Johanning, Oberhausen (DE); Daniela Dostal, Dortmund (DE)

(73) Assignees: THYSSENKRUPP INDUSTRIAL SOLUTIONS AG, Essen (DE); THYSSENKRUPP AG, Essen (DE)

( * ) Notice: Subject to any disclaimer, the term of this patent is extended or adjusted under 35 U.S.C. 154(b) by 0 days.

(21) Appl. No.: 15/780,867

(22) PCT Filed: Dec. 8, 2016

(86) PCT No.: PCT/EP2016/080275
§ 371 (c)(1),
(2) Date: Jun. 1, 2018

(87) PCT Pub. No.: WO2017/102546
PCT Pub. Date: Jun. 22, 2017

(65) Prior Publication Data
US 2018/0282265 A1    Oct. 4, 2018

(30) Foreign Application Priority Data
Dec. 14, 2015   (DE) .................. 10 2015 121 756

(51) Int. Cl.
*C01B 3/02*    (2006.01)
*C01C 1/04*    (2006.01)
(Continued)

(52) U.S. Cl.
CPC ............ *C07C 273/10* (2013.01); *C01B 3/025* (2013.01); *C01C 1/0405* (2013.01);
(Continued)

(58) Field of Classification Search
None
See application file for complete search history.

(56) References Cited

U.S. PATENT DOCUMENTS 4,690,812 A * 9/1987 Ranke .................. C07C 273/10
423/359
4,988,491 A * 1/1991 Van Dijk ................ C01B 3/025
423/356
(Continued)

FOREIGN PATENT DOCUMENTS

CA       1238651 A1 *  6/1988
DE       1668547 A      9/1971
(Continued)

OTHER PUBLICATIONS

S. Kawasumi, Equilibrium of the CO2—NH3—H2O-Urea System under High Temperature and Pressure. III. Effect of Water Added on Vapor-Liquid Equilibrium, Bull. Chem. Soc. Jap, vol. 26 (1953), No. 5, pp. 218-222.
(Continued)

*Primary Examiner* — Amy C Bonaparte
(74) *Attorney, Agent, or Firm* — Thyssenkrupp North America, Inc.

(57) ABSTRACT

Processes for separating carbon dioxide from CO2-containing gases and an apparatus for providing carbon dioxide for the synthesis of urea.

10 Claims, 1 Drawing Sheet

(51) Int. Cl.
*B01D 53/14* (2006.01)
*C07C 273/10* (2006.01)

(52) U.S. Cl.
CPC .. *B01D 53/1475* (2013.01); *C01B 2203/0415* (2013.01); *C01B 2203/0475* (2013.01); *Y02P 20/52* (2015.11)

(56) References Cited

U.S. PATENT DOCUMENTS

| | | |
|---|---|---|
| 6,448,441 B1 | 9/2002 | Wing-Chiu |
| 2014/0364647 A1 | 12/2014 | Iaquaniello |

FOREIGN PATENT DOCUMENTS

| | | |
|---|---|---|
| DE | 2613102 A | 10/1976 |
| DE | 3239605 A | 4/1984 |
| EP | 0150030 A | 7/1985 |
| WO | 2015086149 A | 6/2015 |

OTHER PUBLICATIONS

A. Nielsen, I. Dybkjaer, Ammonia—Catalysis and Manufacture, Springer Berlin 1995, chapter 6, pp. 199-327.
M. Appl, Ammonia. Principles and Industrial Practice, WILEY-VCH Verlag GmbH 1999.
English Translation of International Search Report issued in PCT/EP2016/080275 dated Feb. 15, 2017 (dated Feb. 23, 2017).

\* cited by examiner

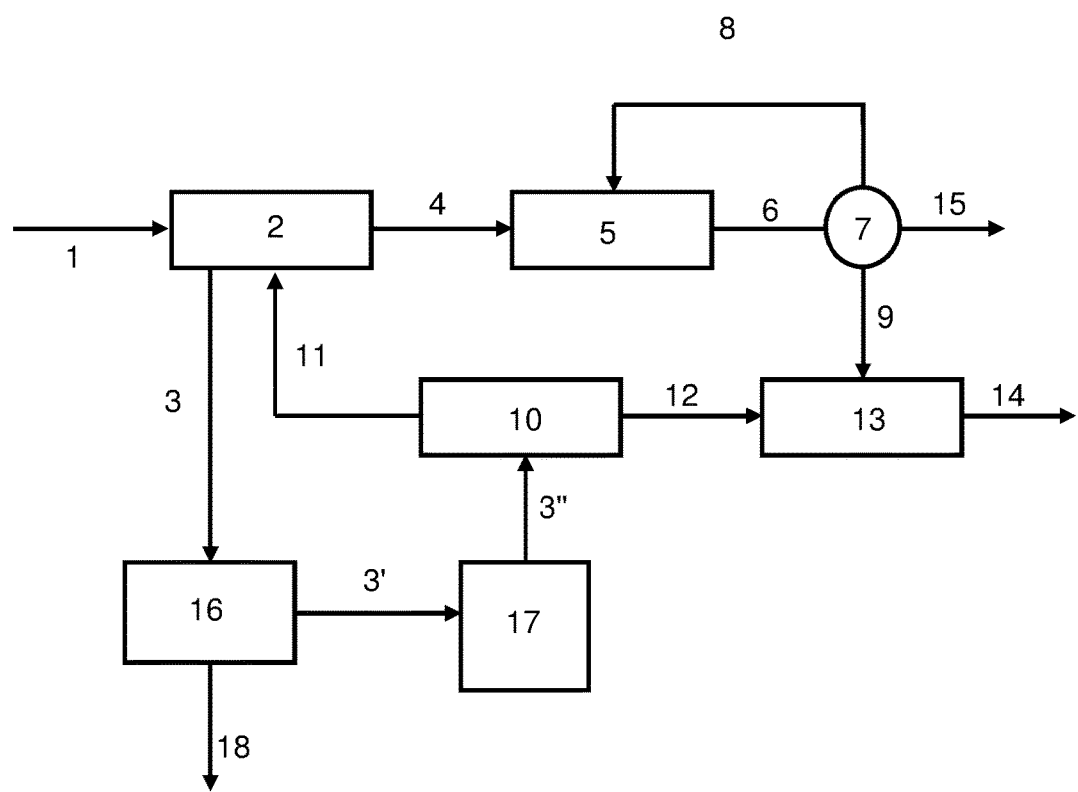

METHOD FOR THE PROVISION OF CARBON DIOXIDE FOR THE SYNTHESIS OF UREA

CROSS REFERENCE TO RELATED APPLICATIONS

This application is a U.S. National Stage Entry of International Patent Application Serial Number PCT/EP2016/080275, filed Dec. 8, 2016, which claims priority to German Patent Application No. DE 10 2015 121 756.2, filed Dec. 14, 2015, the entire contents of both of which are incorporated herein by reference.

FIELD

The present disclosure generally relates to a process for separating carbon dioxide from $CO_2$-containing gases and an apparatus for providing carbon dioxide for the synthesis of urea.

BACKGROUND

The industrial preparation of urea is at present based virtually exclusively on the high-pressure synthesis from ammonia and carbon dioxide in a urea plant at about 150 bar and about 180° C.

The two starting materials for the urea synthesis are generally provided in an ammonia plant which is usually in the direct vicinity of the urea plant concerned. The carbon dioxide required for the urea synthesis is obtained in the synthesis gas production of the ammonia plant as constituent of the crude synthesis gas after reforming. Since carbon dioxide would act as catalyst poison in the ammonia synthesis, it has to be separated off from the synthesis gas. In the prior art, the use of regenerative gas scrubs, for which there is a relatively large number of selectively acting solvents available, is known for this purpose.

Since ammonia is generally present in liquid form at the battery limits of the ammonia plant, it can be brought to the pressure level of the urea plant only with a limited outlay in terms of energy and apparatus. However, the carbon dioxide is obtained in gaseous form in the ammonia plant. For this reason, a disproportionately large outlay in terms of energy and apparatus is required for increasing the pressure in order to bring the carbon dioxide to the pressure level of the urea plant.

The integration of ammonia and urea plants, in which the carbon dioxide is separated off using ammonia or ammonia/water mixtures, is known in the prior art. The carbon dioxide is predominantly bound chemically in the form of carbamate ions and carbonate ions in the solution and can then likewise be introduced into the urea synthesis with a comparatively low outlay by pumping.

In the past, various concepts for process-side integration of ammonia and urea plants have been proposed in order to reduce the total energy requirement for $CO_2$ compression and also the overall outlay in terms of apparatus for the plant. A similar aspect of all these concepts is that the entire amount of $CO_2$ is removed from the synthesis gas by means of ammonia intrinsic to the process and the mixture formed is passed without further work-up to the urea synthesis. This is referred to as a "fully integrated ammonia-urea complex".

DE 1 668 547 discloses a process for preparing ammonia and urea which is characterized in that ammonia synthesis gas containing carbon dioxide, nitrogen and hydrogen is introduced into a first zone which is kept under such conditions that carbon dioxide is separated off from the synthesis gas in an ammonia-containing liquid and a condensate containing ammonium carbamate is obtained and in that the remaining ammonia synthesis gas is introduced into an ammonia synthesis zone and the condensate is introduced into a second zone which is maintained under conditions suitable for the preparation of urea from the condensate. This is a typical example of a fully integrated process, and no direct isolation of $CO_2$ takes place here.

DE 26 13 102 C2 discloses a process for the simultaneous preparation of ammonia and urea, in which a gas mixture which is composed of carbon dioxide, nitrogen and hydrogen and has been obtained in the reforming of hydrocarbons and subsequent CO conversion is fed to an absorption of the carbon dioxide by means of ammonia solution which is obtained in an absorption of the ammonia from the ammonia synthesis by means of water and the ammonium carbamate solution formed in this way is introduced into the urea synthesis.

In both these processes, the ammonium carbamate solutions are passed directly to the synthesis of urea. However, detailed studies have shown that it is not possible to realize an energetically favorable overall solution in this way. The synthesis of urea from ammonia and carbon dioxide is exothermic overall. It consists of the relatively strong exothermic and comparatively fast reaction of the starting materials to form ammonium carbamate and the significantly slower and endothermic decomposition of the carbamate to form urea and water. Good energy efficiency of the overall process can be achieved only when the heat of reaction liberated in the carbamate formation reaction is utilized for the formation of urea.

In addition, it is a fact that the start-up of an integrated plant made up of ammonia and urea plants is complex and separate operation of ammonia or urea plant would not be feasible.

A large quantity of heat is liberated in carbamate formation in a $CO_2$ scrub using ammonia or ammonia/water mixtures. Water could take up the heat much more effectively than ammonia, but is present only in small amounts, if at all. Cooling therefore has to be employed to hold back the ammonia. However, in the concepts proposed hitherto, this heat mostly has to be removed unutilized by means of cooling water. The quantity of heat required by the urea reactor then has to be additionally provided and the energy balance of the process becomes more unfavorable. Furthermore, a considerable additional quantity of water is introduced with the carbamate stream into the urea synthesis in the processes described in the prior art, as a result of which the equilibrium of the urea formation reaction is adversely affected. Without additional introduction of water, the urea yield is in the ideal case about 45%. Each additional introduced water molecule decreases the yield. Comprehensive information may be found in the literature, e.g. in S. Kawasumi, Equilibrium of the $CO_2$—$NH_3$—$H_2O$-Urea System under High Temperature and Pressure. III. Effect of Water Added on Vapor-Liquid Equilibrium, *Bull. Chem. Soc. Jap*, Vol 26 (1953), No. 5, pp. 218-222.

DE 32 39 605 A1 discloses a process for the combined preparation of ammonia and urea, in which the ammonia synthesis gas consisting essentially of hydrogen, nitrogen and carbon dioxide is subjected to a pressure scrub at temperatures of not more than ambient temperature in order to remove acidic impurities, in particular carbon dioxide, using a physically acting solvent, whereupon the loaded solvent is partially depressurized to effect outgassing of inerts and subsequently regenerated at atmospheric pressure and recirculated to the pressure scrub and the carbon dioxide liberated in the regeneration is employed for the urea synthesis. However, this process makes only a small reduction in the work of compression possible. In addition, only part of the carbon dioxide is liberated from the solvent at a relatively high pressure in this process. A $CO_2$ compressor is therefore also still necessary in this process.

Thus a need exists for improved processes and apparatuses for preparing urea in a fully integrated plant having a nominal output of, for example, 1000 metric tons per day.

BRIEF DESCRIPTION OF THE FIGURE

FIG. 1 is a diagram of the flow paths in the apparatus of the invention.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting 'a' element or 'an' element in the appended claims does not restrict those claims to articles, apparatuses, systems, methods, or the like having only one of that element, even where other elements in the same claim or different claims are preceded by 'at least one' or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The invention relates to a process for separating carbon dioxide from CO2-containing gases and an apparatus for providing carbon dioxide for the synthesis of urea.

A first aspect of the invention relates to a process for providing $CO_2$ for the synthesis of urea and for preparing urea, wherein the process comprises the following steps:
a) provision of a gas stream A comprising hydrogen, nitrogen and carbon dioxide;
b) removal of at least part of the carbon dioxide of the gas stream A by means of a solvent to form a carbon dioxide-depleted gas stream B and a solvent loaded with carbon dioxide;
c) synthesis of ammonia from at least part of the hydrogen and at least part of the nitrogen which are present in the gas stream B;
d) desorption of the carbon dioxide from the loaded solvent from step (b); and
e) synthesis of urea from at least part of the ammonia synthesized in step (c) and at least part of the carbon dioxide desorbed in step (d);
where the desorption of the carbon dioxide in step (d) is carried out at a higher pressure than the synthesis of the urea in step (e).

In step (a) of the process of the invention, a gas stream A comprising mainly hydrogen, nitrogen and carbon dioxide is provided. The gas stream A can optionally comprise preferably inert components such as methane, argon, carbon monoxide and/or helium. The gas stream A is preferably obtained as synthesis gas from hydrocarbons, preferably from natural gas, water in the form of steam and air or oxygen by reforming and subsequent gas purification. Suitable processes for producing such a synthesis gas are known to those skilled in the art and comprehensive reference can in this respect be made to, for example, A. Nielsen, I. Dybkjaer, *Ammonia—Catalysis and Manufacture*, Springer Berlin 1995, chapter 6, pages 202-326; M. Appl, Ammonia. Principles and Industrial Practice, WILEY-VCH Verlag GmbH 1999. In a preferred embodiment, at least part of the gas stream A is provided by steam reforming and/or by autothermal reforming.

The gas stream A provided in step (a) of the process of the invention can, as synthesis gas, have previously been subjected to conventional treatment measures, e.g. helium removal, natural gas desulfurization and/or conversion of carbon monoxide into carbon dioxide.

In step (b) of the process of the invention, at least part of the carbon dioxide of the gas stream A is removed by means of a solvent to form a carbon dioxide-depleted gas stream B and a solvent loaded with carbon dioxide. Here, the gas stream may have to be cooled to temperatures of 30-70° C.

In a preferred embodiment, the solvent by means of which the carbon dioxide is separated off in step (b) is an ammonia/water mixture. The proportion of ammonia in the ammonia/water mixture is preferably in the range from 1 to 50% by weight, more preferably in the range from 5 to 45% by weight, in the range from 10 to 40% by weight, in the range from 15 to 35% by weight, in the range from 20 to 30% by weight and particularly preferably in the range from 20 to 25% by weight. In an ammonia/water mixture, the carbon dioxide is preferably chemically bound in the form of carbamate and/or carbonate ions.

In step (c) of the process of the invention, ammonia is synthesized from at least part of the hydrogen and at least part of the nitrogen which are present in the gas stream B. For this purpose, the gas stream B is introduced into an ammonia reactor. The gas stream B may still comprise residues of carbon dioxide and/or carbon monoxide, which are preferably separated off by, for example, cryogenic methods or by pressure swing absorption from the gas stream B before the synthesis of ammonia. These residues are preferably converted by methanation into methane. Suitable processes for hydrogenating carbon monoxide and carbon dioxide to form methane are known to those skilled in the art. The methanation reduces the content of carbon monoxide, and optionally also carbon dioxide, in the gas stream B and increases the content of methane in the gas stream. The gas stream B is optionally compressed to an increased pressure, preferably to a pressure in the range from 120 to 250 bar, more preferably in the range from 180 to 220 bar, before the ammonia synthesis. The ammonia reactor preferably comprises at least one catalyst bed through which the gas stream B flows not purely axially but predominantly radially, preferably from the outside inward. At least part of the ammonia formed in the ammonia reactor is then preferably separated from the resulting product stream by cooling, for which purpose the gas stream preferably passes through firstly a heat exchanger and subsequently a condensation apparatus. Here, the gas stream is cooled, preferably to temperatures in the range from −15° C. to −79°, more preferably in the range from −25° C. to −79° C., in the range from −35° C. to −79° C. or in the range from −35° C. to −50° C., so that ammonia can be condensed out under the conditions indicated and in this way be separated from the gas phase by phase separation.

In a preferred embodiment, the solvent loaded with carbon dioxide is at least partially depressurized after step (b) and before step (d) in order to remove components, such as e.g. hydrogen and nitrogen, which have been coabsorbed in step (b) from the solvent. For this purpose, the solvent loaded with carbon dioxide is, after step (b), conveyed through an intermediate depressurizing stage (flash) to remove inerts. A hydroturbine can be used for recovering energy in the depressurization of the loaded solvent. The solvent loaded with carbon dioxide is preferably depressurized to a pressure below 10 bar after step (b) and before step (d). This solution is used industrially at comparable places and is known to a person skilled in the art.

The depressurized solution which is still loaded with $CO_2$ is compressed by means of a pump. The target pressure should preferably be above the urea synthesis pressure and be sufficiently high to compensate for the pressure drops in the heat exchanger, in the desorption column and in the pipes. In practice, the pressure drops will normally not exceed values of not more than 30 bar. In another preferred embodiment, the target pressure should be at least so far above the urea synthesis pressure that $CO_2$ can be introduced, preferably without further compression, into the urea synthesis despite the pressure drops in the pipes, regulating valves and apparatuses located in the flow path between the pump and the urea synthesis. The target pressure is preferably at least 1 bar, more preferably at least 2 bar, at least 4 bar, at least 6 bar, at least 8 bar, at least 10 bar, at least 20 bar or at least 30 bar, above the urea synthesis pressure. In another preferred embodiment, the target pressure is so far above the urea synthesis pressure that the pressure difference between target pressure and the urea synthesis pressure is in the range from 1 to 40 bar, more preferably in the range from 2 to 30 bar or in the range from 5 to 20 bar.

In step (d) of the process of the invention, the carbon dioxide is desorbed from the solvent in a suitable desorption apparatus, preferably in a desorption column which is preferably configured as rectification column. Desorption is preferably effected by heating of the solvent, which preferably has a boiling point higher than that of carbon dioxide. The desorption of the carbon dioxide is preferably carried out at a higher pressure than the synthesis of the urea in step (e) and the pressure difference between the pressure at which desorption is carried out and the pressure at which urea is synthesized in step (e) is preferably sufficiently high to compensate for any pressure drops of the carbon dioxide occurring on the way to the urea synthesis. The pressure at which the desorption of carbon dioxide is carried out is preferably at least 1 bar higher than the pressure at which the urea is synthesized, more preferably at least 2 bar, at least 4 bar, at least 6 bar, at least 8 bar, at least 10 bar, at least 20 bar or at least 30 bar. In another preferred embodiment, the desorption of the carbon dioxide is carried out at a pressure which is above the urea synthesis pressure, so that the pressure difference between the desorption of carbon dioxide and the urea synthesis pressure is in the range from 1 to 40 bar, more preferably in the range from 2 to 30 bar or in the range from 5 to 20 bar. The temperature at which the desorption is carried out in step (d) is preferably selected so that the carbon dioxide can desorb at the pressure prevailing in each case. The temperature is determined by the specific urea synthesis pressure and the necessary overpressure for overcoming the pressure drops. The urea synthesis pressure is typically at least 120 bar to 150 bar and the overpressure is preferably at least 1 bar, more preferably at least 2 bar, at least 3 bar, at least 4 bar, at least 5 bar, at least 6 bar, at least 8 bar, at least 10 bar, at least 20 bar or at least 30 bar. In a preferred embodiment, the desorption of the carbon dioxide is carried out at a temperature in the range from 100° C. to 300° C., more preferably in the range from 130° C. to 270° C., in the range from 150° C. to 250° C. or in the range from 170 to 230° C.

In step (e) of the process of the invention, urea is synthesized from at least part of the ammonia synthesized in step (c) and at least part of the carbon dioxide desorbed in step (d). For this purpose, the ammonia synthesized in step (c) is firstly preferably compressed, preferably to a pressure of at least 100 bar, more preferably to a pressure of at least 120 bar, at least 140 bar or at least 150 bar.

The synthesis of urea is preferably carried out at a pressure in the range from 100 to 300 bar, more preferably in the range from 120 to 200 bar or in the range from 140 to 160 bar. The product produced in step (e) comprises essentially urea, water and ammonium carbamate and possibly also unreacted ammonia and carbon dioxide. The ammonium carbamate and the ammonia and also the carbon dioxide have to be removed from the solution and can then be provided again for the reaction process for the synthesis of urea. The removal is usually achieved by stripping with $CO_2$ or $NH_3$. These processes are known in the prior art for urea plants and to a person skilled in the art. The synthesis of urea is preferably carried out in a conventional urea plant, the structure of which is known to a person skilled in the art.

The desorption of the carbon dioxide in step (d) is carried out at a higher pressure than the synthesis of the urea in step (e). The desorption of the carbon dioxide in step (d) is preferably carried out at a pressure which is at least 1 bar higher than the pressure at which the urea is synthesized, more preferably at least 2 bar, at least 3 bar, at least 4 bar, at least 5 bar, at least 6 bar, at least 10 bar, at least 20 bar, at least 30 bar, preferably a pressure of at least 120 bar, more preferably at least 140 bar. In another preferred embodiment, the desorption of the carbon dioxide is carried out at a pressure which is above the urea synthesis pressure so that the pressure difference between the pressure at which the desorption of carbon dioxide is carried out and the urea synthesis pressure is in the range from 1 to 40 bar, more preferably in the range from 2 to 30 bar or in the range from 5 to 20 bar. The carbon dioxide can preferably be fed directly to the urea synthesis in step (e) without further compression after desorption in step (d).

It has surprisingly been found that the carbon dioxide can be desorbed with the required purity from the solvent by means of a still moderate temperature level. However, the required temperature level is, at about 200° C., so high that the concept using conventional solvents could not be realized because of the limited thermostability of the solvents. Owing to the relatively high vapor pressure even at moderate temperatures and the relatively high heat of desorption, the use of ammonia in this form as pure solvent in a gas scrub is therefore not obvious. In addition, an additional introduction of water with the carbon dioxide into the urea synthesis can be largely avoided in the process of the invention, in contrast to known disclosures (cf., for example, DE 1 668 547 or DE 26 13 102 C2).

In a preferred embodiment, the energy required for desorption of the carbon dioxide in step (d) is provided by steam which is generated, for example, in the synthesis of ammonia. In a preferred embodiment, the steam which is to be used in the desorption of the carbon dioxide is produced by means of the process heat liberated in the synthesis of ammonia. The steam is in this case preferably passed through a heat exchanger and as a result transfers part of the energy required for desorption to the carbon dioxide-containing solvent.

It has surprisingly been found that the quantity of heat required for the desorption of the carbon dioxide in step (d) and the quantity of heat required for the removal of the carbon dioxide in step (b) can be made available by means of limited modifications to the steam system in combined ammonia-urea plants. Since the desorption of the carbon dioxide in step (d) occurs at a higher pressure than the synthesis of the urea in step (e), the carbon dioxide liberated after desorption can be used without further compression for synthesizing the urea, as a result of which a carbon dioxide compressor can be saved. Since the steam consumption for driving the carbon dioxide compressor is dispensed with, there is overall a significant reduction in the energy consumption.

Under the assumptions that
the urea plant remains largely unchanged,
the removal of the carbon dioxide by means of ammonia or ammonia/water solutions requires a similar outlay in terms of apparatus as the carbon dioxide scrubs which correspond to the prior art and are used in presently erected ammonia plants and
the modifications to the steam system are largely cost neutral, the omission of the carbon dioxide compressor including its auxiliary apparatuses (drive turbine, intermediate cooler, oil system, etc.) results in a substantial reduction in the capital costs of the plant.

Separate operation of the ammonia plant without urea plant is also possible in the case of this concept since the carbon dioxide which has been separated off is depressurized with minimal outlay and can then be released into the surroundings, as in a conventional process. Only sole operation of the urea plant would no longer be readily achievable without additional facilities for provision of the carbon dioxide at the urea synthesis pressure level.

In a preferred embodiment, the synthesis of the urea in step (e) comprises the subreactions (i) and (ii):
(i) formation of ammonium carbamate from ammonia and carbon dioxide; and
(ii) conversion of the ammonium carbamate into urea and water;
where the energy for the endothermic subreaction (ii) is obtained at least partly from the exothermic subreaction (i).

The two subreactions are, because of the size of the apparatuses, preferably but not necessarily carried out in separate reaction apparatuses which are preferably arranged in the immediate vicinity of one another, so that the heat liberated in the formation of ammonium carbamate from ammonia and carbon dioxide can largely be used without loss for the dehydration of the ammonium carbamate. In this way, it is possible to realize an energetically favorable overall solution since the heat of reaction of the carbamate formation reaction is utilized for urea formation and is not removed unutilized by means of cooling water.

A further aspect of the invention relates to an apparatus for preparing urea, wherein the apparatus comprises the following interacting components:
(A) apparatus for providing a gas stream comprising hydrogen, nitrogen and carbon dioxide;
(B) means for removing at least part of the carbon dioxide of the gas stream by means of a solvent;
(C) ammonia synthesis unit comprising an ammonia reactor for the synthesis of ammonia from at least part of the hydrogen and at least part of the nitrogen which are present in the gas stream;
(D) means for desorbing the carbon dioxide from the solvent; and
(E) urea synthesis unit comprising a urea reactor for the synthesis of urea from at least part of the ammonia synthesized in the ammonia synthesis unit and at least part of the carbon dioxide desorbed from the solvent;

where the means for desorbing the carbon dioxide are operated at a higher pressure than the urea synthesis unit.

All preferred embodiments described in connection with the process of the invention apply analogously to the apparatus of the invention and will therefore not be repeated at this point.

The apparatus of the invention comprises an apparatus for providing a gas stream comprising hydrogen, nitrogen, carbon dioxide and optionally further inert components. The apparatus for providing a gas stream preferably comprises a steam reformer and/or an autothermal reformer. If the apparatus comprises an autothermal reformer, the amount of carbon dioxide which is formed in the autothermal reformer can be controlled by varying reaction parameters such as the pressure or the steam/carbon ratio. Preference is given to just such an amount of carbon dioxide that the ammonia produced in the apparatus for preparing ammonia can be reacted, preferably completely, with carbon dioxide to form urea.

Furthermore, the apparatus of the invention comprises means for removing at least part of the carbon dioxide by means of a solvent. The means for removing at least part of the carbon dioxide preferably comprises an ammonia-water scrub.

The apparatus of the invention further comprises an ammonia synthesis unit comprising an ammonia reactor for synthesizing ammonia from at least part of the hydrogen and at least part of the nitrogen present in the gas stream. The ammonia reactor preferably comprises at least one catalyst bed through which the gas stream preferably flows not purely axially but predominantly radially, preferably from the outside inward.

In addition, the apparatus of the invention comprises means for desorbing the carbon dioxide from the solvent. For example, the means for desorption can comprise a distillation column. The means for desorbing the carbon dioxide, in particular the distillation column, are preferably operated at a pressure which is above the pressure at which the urea synthesis unit is operated and is sufficiently high to overcome the pressure drops of the carbon dioxide up to entry into the urea synthesis. The pressure at which the means for desorbing the carbon dioxide are operated is preferably at least 1 bar higher than the pressure at which the urea synthesis unit is operated, more preferably at least 2 bar, at least 3 bar, at least 4 bar, at least 5 bar, at least 6 bar, at least 8 bar, at least 10 bar, at least 20 bar or at least 30 bar. The means for desorbing the carbon dioxide are preferably operated at a pressure of at least 120 bar, more preferably at least 150 bar. In another preferred embodiment, the means for desorbing the carbon dioxide are operated at a higher pressure than the urea synthesis unit so that the pressure difference between the pressure at which the means for desorbing the carbon dioxide are operated and the pressure at which the urea synthesis unit is operated is in the range from 1 to 40 bar, more preferably in the range from 2 to 30 bar or in the range from 5 to 20 bar.

The apparatus of the invention further comprises a urea synthesis unit. The urea synthesis unit preferably comprises two spatially separate reaction chambers, with the reaction of carbon dioxide and ammonia to form ammonium carbamate preferably taking place in a first reaction chamber and the dehydration of the ammonium carbamate preferably taking place in a second reaction chamber.

The means for desorbing the carbon dioxide are preferably operated at a pressure which is above the pressure at which the urea synthesis unit is operated and the pressure difference between the pressure at which the means for desorbing the carbon dioxide and the pressure at which the urea synthesis unit are operated is sufficiently high to compensate for any pressure drops of the carbon dioxide occurring before entry into the urea synthesis unit. The means for desorbing the carbon dioxide are preferably operated at a pressure which is at least 1 bar above the pressure at which the urea synthesis unit is operated, more preferably at least 2 bar, at least 3 bar, at least 4 bar, at least 5 bar, at least 6 bar, at least 8 bar, at least 10 bar, at least 20 bar or at least 30 bar. In another preferred embodiment, the means for desorbing the carbon dioxide are operated at a higher pressure than the urea synthesis unit so that the pressure difference between the pressure at which the means for desorbing the carbon dioxide are operated and the pressure at which the urea synthesis unit is operated is in the range from 1 to 40 bar, more preferably in the range from 2 to 30 bar or in the range from 5 to 20 bar. Accordingly, preference is given to no further means for compressing the carbon dioxide being arranged between the means for desorbing the carbon dioxide and the urea synthesis unit.

The apparatus of the invention is particularly suitable for carrying out the process of the invention. A further aspect of the invention therefore relates to the use of the apparatus of the invention in the process of the invention.

A gas stream A (1), which comprises hydrogen, nitrogen, carbon monoxide, carbon dioxide and possibly further components which are inert in respect of the ammonia synthesis unit, e.g. methane or argon, is preferably provided in a steam reformer, optionally an autothermal reformer. At least part of the carbon dioxide present in the gas stream A (1) is removed in a separation apparatus (2), preferably by means of an ammonia-water scrub. The carbon dioxide-depleted gas stream B (4) formed here is fed to an ammonia synthesis unit (5) in which at least part of the hydrogen and at least part of the nitrogen of the gas stream B (4) are converted into ammonia. A product stream (6) which comprises predominantly ammonia, hydrogen and nitrogen is discharged from the ammonia synthesis unit (5). At least part of the ammonia of the product stream (6) is separated off in an ammonia removal apparatus (7) and fed as ammonia stream (9) to the urea synthesis unit (13). At least part of the ammonia can optionally be compressed after discharge from the ammonia removal apparatus (7). The ammonia-depleted product stream (8) is recirculated to the ammonia synthesis unit (5). Any excess ammonia stream (15) can be passed to a further use, as corresponds to the prior art.

The carbon dioxide-enriched solvent (3) leaving the separation apparatus (2) is optionally firstly introduced into an intermediate depressurization stage (16) in which any components (18) which have been coabsorbed in the separation apparatus (2) are removed from the solvent. The carbon dioxide-enriched solvent (3') is preferably compressed by means of a pump (17), with the target pressure preferably being from 1 bar to 30 bar above the urea synthesis pressure. The carbon dioxide-enriched and compressed solvent (3") is subsequently fed to a desorption apparatus (10) in which the carbon dioxide (12) is desorbed from the solvent stream (3"), preferably at a pressure which is above the operating pressure of the urea synthesis unit (13). The regenerated solvent stream (11) which is discharged from the desorption apparatus (10) can be reused in the separation apparatus (2). At least part of the carbon dioxide stream (12) which is desorbed in the desorption apparatus (10) is fed into the urea synthesis unit (13) and reacted there with the ammonia stream (9) to form urea. The urea stream (14) leaves the urea synthesis unit (13) and is optionally processed further.

What is claimed is:

1. A process for preparing urea, comprising:
providing a gas stream comprising hydrogen, nitrogen and carbon dioxide;
removing, with a solvent, at least part of the carbon dioxide of the gas stream to form a carbon dioxide-depleted gas stream;
synthesizing ammonia from at least part of the hydrogen and at least part of the nitrogen which are present in the carbon dioxide-depleted gas stream;
desorbing the carbon dioxide from the solvent; and
synthesizing urea from at least part of the ammonia from said synthesizing step and at least part of the carbon dioxide from said desorbing step;
wherein the desorbing of the carbon dioxide in said desorbing step is carried out at a higher pressure than the synthesizing of the urea in said synthesizing step.

2. The process of claim 1, wherein the solvent loaded with carbon dioxide is at least partially depressurized after said removing step and before said desorbing step in order to remove components which have been co-absorbed in said removing step from the solvent.

3. The process of claim 1, wherein the desorption of the carbon dioxide in said desorbing step is carried out at a higher pressure than the synthesis of the urea in said synthesizing step and the pressure difference between the pressure at which desorption is carried out and the pressure at which urea is synthesized in said synthesizing step is sufficiently high to compensate for any pressure drops of the carbon dioxide occurring before entry into the urea synthesis.

4. The process of claim 1, wherein the temperature at which said desorbing step is carried out is selected so that the carbon dioxide can desorb at the the desorbing step.

5. The process of claim 1, wherein the solvent by which the carbon dioxide is separated off in said removing step comprises an ammonia/water mixture.

6. The process of claim 1, wherein the desorption of the carbon dioxide in said desorbing step is carried out at a temperature in the range from about 130° C. to 270° C.

7. The process of claim 1, wherein the energy required for desorption of the carbon dioxide in said desorbing step is provided by steam.

8. The process as claimed in claim 7, wherein the steam is produced by process heat liberated in the synthesis of ammonia.

9. The process of claim 1, wherein at least part of the gas stream is provided by one or both of steam reforming and autothermal reforming.

10. The process of claim 1, wherein the synthesis of the urea in said synthesizing step comprises subreactions (i) and (ii):
 (i) formation of ammonium carbamate from ammonia and carbon dioxide; and
 (ii) conversion of the ammonium carbamate into urea and water;
wherein energy for the subreaction (ii) is obtained at least partly from the subreaction (i).

* * * * *